United States Patent [19]
Klemp

[11] Patent Number: 5,536,350
[45] Date of Patent: Jul. 16, 1996

[54] DISPOSABLE GARMENT WITH NOODLE CUFF AND METHOD FOR MANUFACTURING SAME

[75] Inventor: Walter V. Klemp, Houston, Tex.

[73] Assignee: Drypers Corporation, Houston, Tex.

[21] Appl. No.: 312,334

[22] Filed: Sep. 26, 1994

[51] Int. Cl.$^6$ .......................... A61F 13/15; B32B 31/04; B32B 31/14; B32B 31/18
[52] U.S. Cl. ....................... 156/211; 156/227; 604/385.1; 604/385.2
[58] Field of Search .................................. 156/200, 204, 156/211, 227; 2/400; 604/385.1, 385.2

[56] References Cited

U.S. PATENT DOCUMENTS

| | | |
|---|---|---|
| 2,122,417 | 7/1938 | Fridolph . |
| 2,494,307 | 1/1950 | Niolon . |
| 2,829,647 | 4/1958 | Dexter . |
| 2,852,026 | 9/1958 | Karr ................................. 604/385.1 X |
| 3,368,562 | 2/1968 | Vogt . |
| 3,461,871 | 8/1969 | Foote . |
| 3,594,820 | 7/1971 | McCurry . |
| 3,636,953 | 1/1972 | Benevento . |
| 3,794,033 | 2/1974 | Ryan . |
| 3,920,017 | 11/1975 | Karami . |
| 4,216,773 | 8/1980 | Ryan . |
| 4,381,782 | 5/1983 | Mazurak et al. .................. 604/385.2 X |
| 4,410,324 | 10/1983 | Sabee ................. 604/385.2 X |
| 4,500,316 | 2/1985 | Damico ........................... 604/385.1 X |
| 4,519,800 | 5/1985 | Merry .................................... 604/385.2 |
| 4,690,719 | 9/1987 | Lucas . |

FOREIGN PATENT DOCUMENTS

| 2617683 | 1/1989 | France ................................ 604/385.1 |
|---|---|---|

*Primary Examiner*—Adrienne C. Johnstone
*Attorney, Agent, or Firm*—Fulbright & Jaworski

[57] ABSTRACT

A disposable garment and method of manufacturing such whereby profile cuts are made near the longitudinal edges of an absorbent pad assembly to create leg cut-out pieces or noodles. The noodles remain attached to the absorbent pad assembly at a point proximal to a center point of the absorbent pad assembly. The noodles are then folded toward the interior surface of the absorbent pad assembly about the point of attachment and are attached to the interior surface by an adhesive. An outer folding strip of each noodle is then folded back upon the respective noodles and secured to the noodle and the absorbent pad assembly by an adhesive, thereby creating an effective leakage control shield without the need to discard unused material in the manufacturing process.

5 Claims, 4 Drawing Sheets

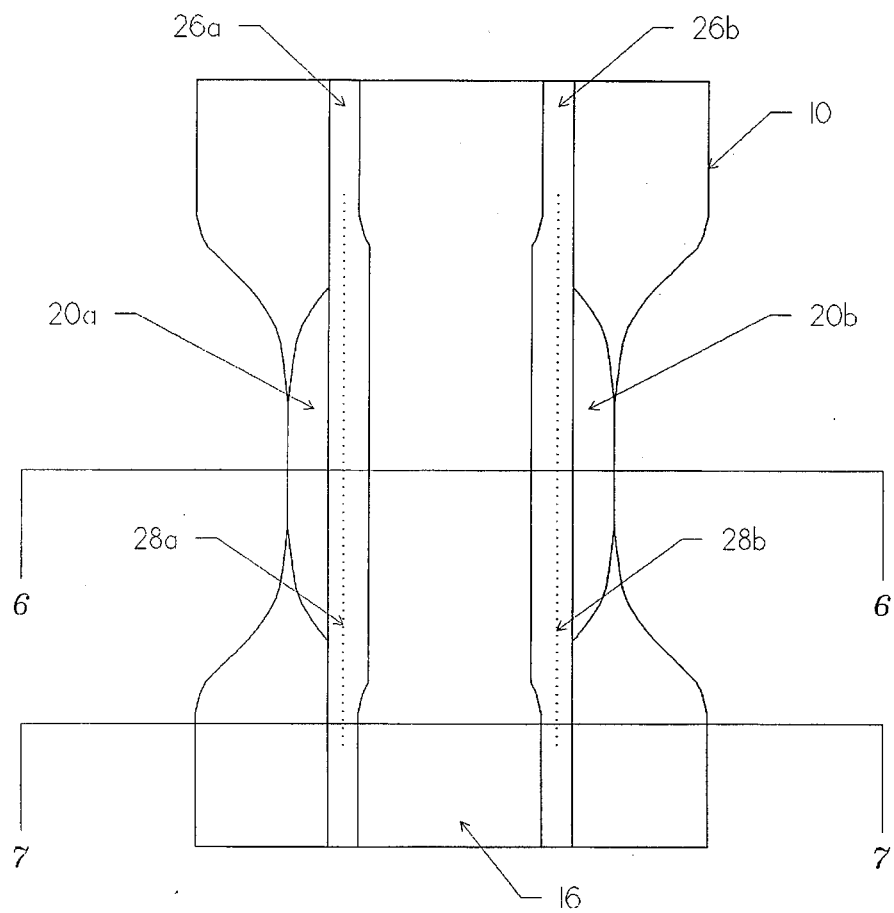
figure 5
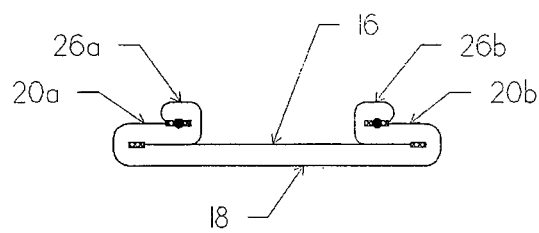 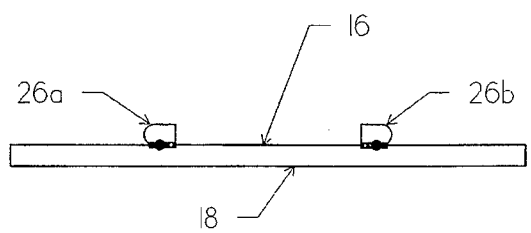
figure 6      figure 7

DISPOSABLE GARMENT WITH NOODLE CUFF AND METHOD FOR MANUFACTURING SAME

BACKGROUND OF THE INVENTION

1. Field of the Invention

The present invention relates to a disposable garment and a method of manufacturing such a disposable garment, and more particularly, to a disposable garment exhibiting a noodle cuff which acts as a leakage control shield, and a method of making such a noodle cuff disposable garment.

2. Description of the Related Technology

A number of disposable garments having a contoured shape have been proposed in the past for use on infants and incontinent adults. The contoured garment generally provides a more comfortable fit than traditional rectangular garments. However, in most cases, such contoured garments are quite expensive to produce due to the use of complex high-precision machinery needed to form the intricate shapes. Many such garments are formed from rectangular absorbent articles, often cut in assembly-line fashion from moving webs. To form a garment from a rectangular piece of absorbent material, material is often cut away from the longitudinal edges of the absorbent article and discarded during formation of the leg holes. Such leg-hole cut-outs are known as "noodles." While the contoured garments generally provide a more comfortable fit, they are prone to leakage along the edges of the contoured region.

For the foregoing reasons, there is a need for a disposable garment that is contoured for a comfortable fit and is constructed to prevent leakage. There is also a need for a method of making a disposable garment wherein waste from discarded material used in the process of making the garment is minimized or eliminated.

SUMMARY OF THE INVENTION

The present invention is directed to a disposable garment having a contoured fit wherein the leg cut-out piece or "noodle" is used as the primary material for construction of a leakage-control shield. The invention is also directed to a method of making a disposable garment which eliminates waste created by discarding unused pieces of material.

A disposable garment having features of the present invention comprises an absorbent pad assembly having longitudinal edges and a noodle formed in each longitudinal edge of the absorbent pad assembly and attached thereto near the center of the absorbent pad assembly. The disposable garment is formed from a rectangular absorbent pad assembly by first partially cutting noodles from the longitudinal edges of the absorbent pad assembly leaving the noodles attached thereto near the center of the absorbent pad. Next, each noodle is folded inwardly toward an interior surface of the absorbent pad assembly about the point of attachment. The noodle exhibits a folding strip along an outer edge thereof which is then folded back over the folded noodle thereby creating a leakage control shield.

The folded noodle and folding strip may be attached to the interior surface of the absorbent pad by an attachment means known to those skilled in the art, such as an adhesive or weldments. An elastic member may also be attached to the folding strip along the longitudinal edge of the absorbent pad assembly by applied adhesive.

It is an object of the present invention to provide a disposable garment having a contoured shape and a leakage control shield along the contoured portion of the garment. It is a further object of the invention to provide a method for manufacturing a disposable garment wherein waste material from discarded pieces of absorbent pad material are minimized or eliminated.

These and other features, aspects, and advantages of the present invention will become better understood with regard to the following description, appended claims, and accompanying drawings.

BRIEF DESCRIPTION OF THE DRAWINGS

FIG. 5 shows a top plan view of the disposable garment shown in FIG. 3 with folding strips folded;

FIG. 6 shows a cross-sectional view of the disposable garment shown in Fig. along the line 6—6;

FIG. 7 shows a cross-sectional view of the disposable garment shown in FIG. 5 along the line 7—7.

DETAILED DESCRIPTION OF THE PREFERRED EMBODIMENTS

Figure 1:
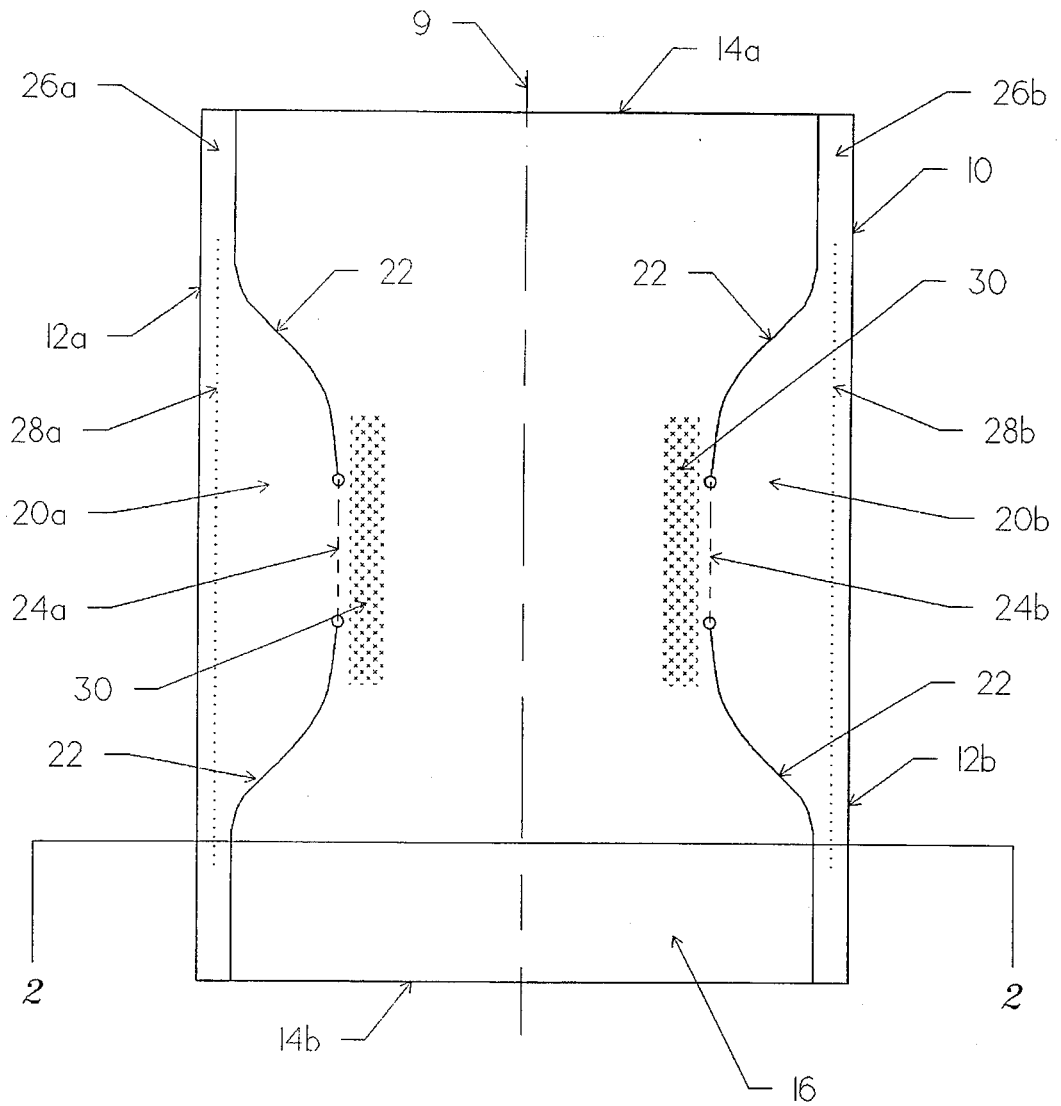
FIG. 1 shows a top plan view of a disposable garment embodying features of the present invention with adhesive 30 applied prior to folding of the noodles.
Figure 2:
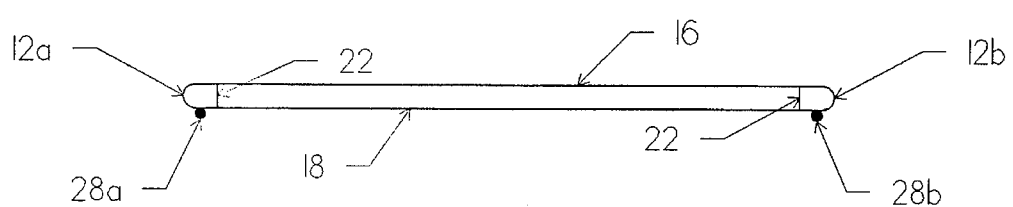
FIG. 2 shows an end view of the disposable garment shown in FIG. 1.

Referring now to FIGS. 1-2, there is shown a disposable garment having an absorbent pad assembly 10, preferably exhibiting a rectangular shape, having longitudinal edges 12a and 12b and lateral edges 14a and 14b connecting the longitudinal edges 12a and 12b, the absorbent pad assembly further exhibiting an interior surface 16 and an exterior surface 18. The absorbent pad assembly 10 is preferably cut from a continuous web along the lateral edges 14a and 14b.

Leg cut-out pieces or noodles 20a and 20b are formed in the longitudinal edges 12a and 12b, respectively, of the absorbent pad assembly 10 by partially cutting along a contoured line 22 near the longitudinal edges 12a and 12b of the absorbent pad assembly 10. The noodles are preferably cut from the absorbent pad assembly along the line 22 such that the noodles 20a and 20b remain attached to the absorbent pad assembly at attachment points 24a and 24b, respectively, proximal to a center point of the absorbent pad assembly 10. The noodles 20a and 20b are preferably formed before the absorbent pad assembly 10 is cut from the web.

The outer edges of noodles 20a and 20b exhibit a folding strip 26a and 26b, respectively, which are each preferably formed of the absorbent pad assembly 10 by cutting along the contoured line 22. Elastic members 28a and 28b are preferably attached to each of the folding strips 26a and 26b, respectively.

Figure 8:
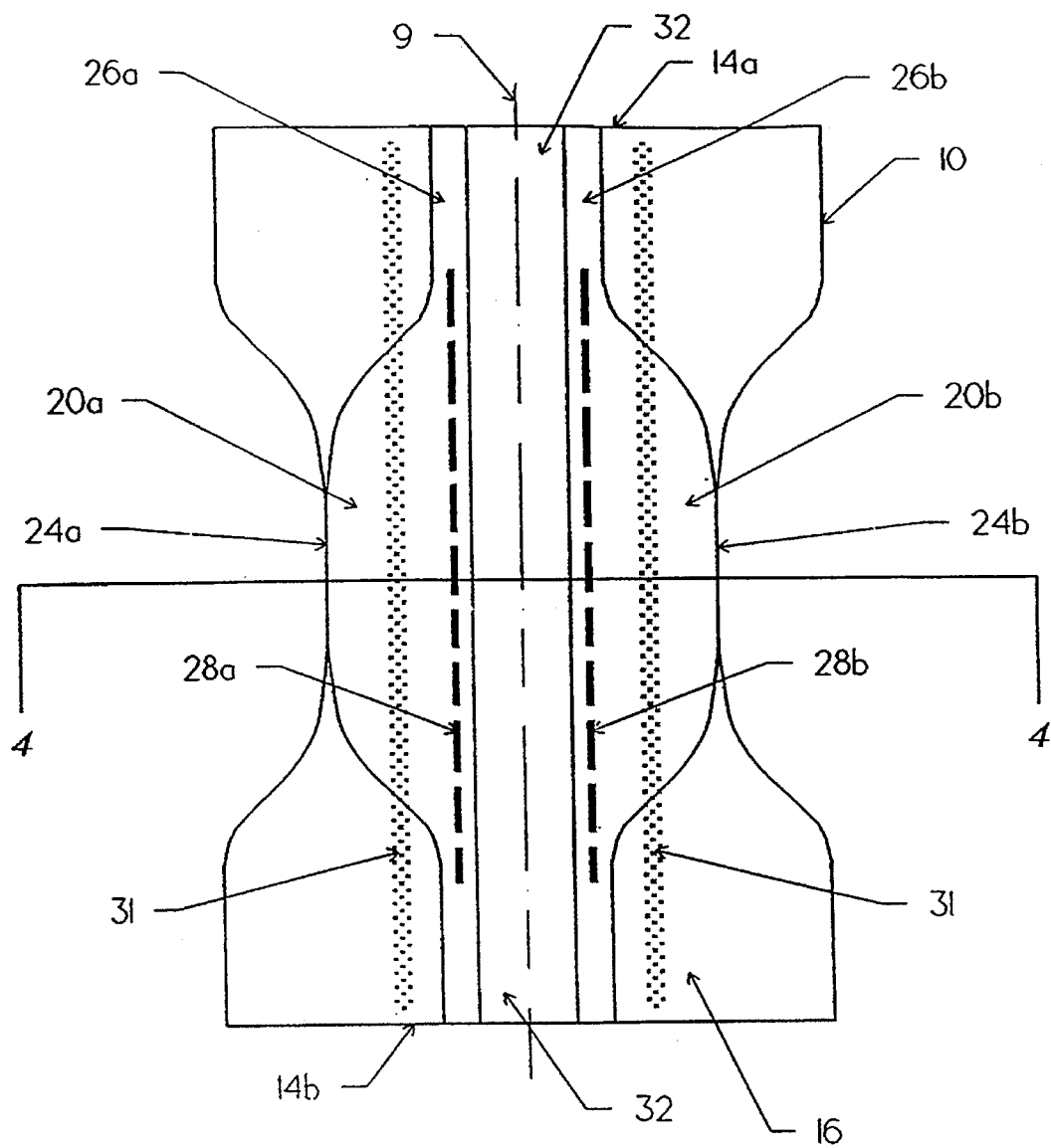
FIG. 8 shows a cross-sectional view of an alternative embodiment of the disposable garment shown in FIG. 3.

The elastic members 28a and 28b help form a leakage-control shield and can be applied to the folding strip in a continuous fashion with applied adhesive, such as glue. The elastic members 28a and 28b may be applied to either the exterior surface 18 or the interior surface 16 of the absorbent pad assembly 10. The elastic members 28a and 28b are preferably applied to the exterior surface 18 of the absorbent pad assembly 10 before the absorbent pad assembly 10 is cut from the web. Preferably, the elastic members 28a and 28b are not adhered near the lateral edges 14a and 14b. Thus, when the absorbent pad assembly 10 is cut from the web, the elastic members 28a and 28b will retract from the lateral edges 14a and 14b as depicted in FIG. 1. In addition, discrete elastic areas along the lengths of elastic strips 28a and 28b may be created by cutting through or macerating the elastic members 28a and 28b at desired points, as depicted in FIG. 8. The elastic members 28a and 28b may be applied as a strip of heated liquid that hardens to an elastic state when cooled or may be any other elasticating substance.

Adhesive may be applied to the interior surface 16 as shown generally by 30. Preferably, adhesive is applied near attachment points 24a and 24b at a location that mirrors the edge of the noodles 20a and 20b. Such application of adhesive facilitates tacking of the noodles 20a and 20b once the noodles are folded toward the centerline 9 of the assembly 10.

Figure 3:
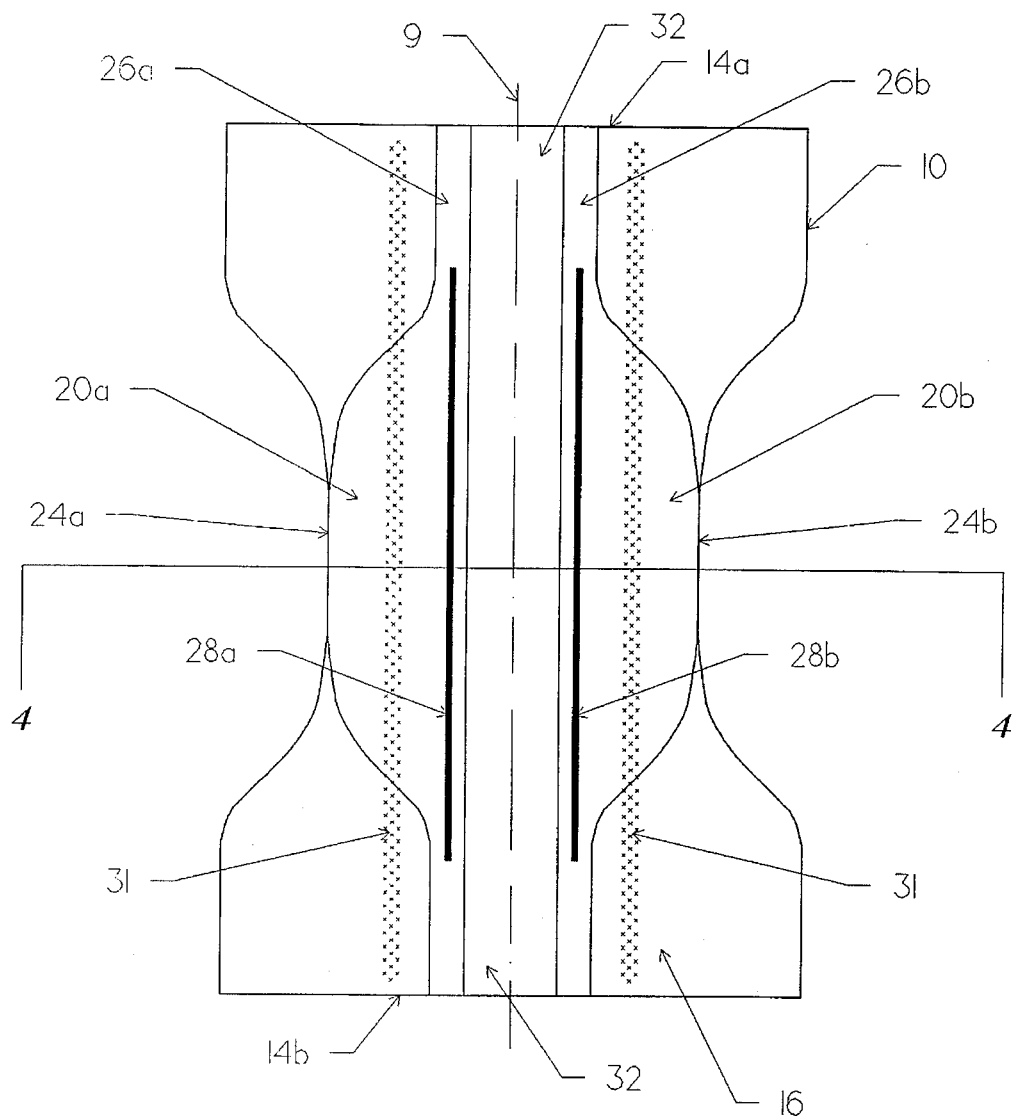
FIG. 3 shows a top plan view of the disposable garment shown in FIG. 1 with the noodles folded inward and with adhesive 31 applied.
Figure 4:
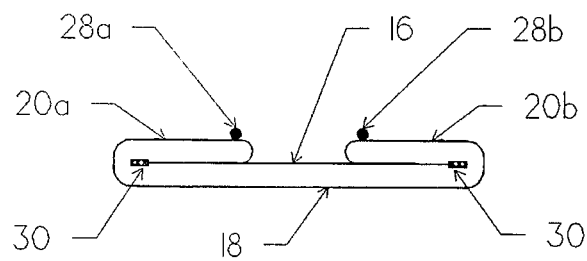
FIG. 4 shows a cross-sectional view of the disposable garment shown in FIG. 3 along the line 4—4.

Once the adhesive 30 has been applied, the noodles 20a and 20b are folded toward the interior surface 16 and centerline 9 of the assembly 10, whereby the noodles 20a and 20b become tacked to the interior 16 of the assembly 10 as depicted in FIG. 3. Such tacking may be affected by other means, such as melting or sonic welding. The noodles 20a and 20b are folded so as to define a trough 32 at the center of the interior surface 16 of the absorbent pad assembly 10.

After the first fold of the noodles 20a and 20b as depicted in FIG. 3, second lines of adhesive 31 are preferably applied to surface 18 of the noodles 20a and 20b and further extending into the interior surface 16 of the absorbent pad assembly 10, in the manner depicted in FIG. 3.

Once the lines of adhesive 31 are applied as depicted in FIG. 3, a second fold of the noodles 20a and 20b may be made. Folding strips 26a and 26b may be folded outward from the centerline 9 of the assembly 10, preferably such that the surface 18 of the folding strips 26a and 26b are tacked back against the noodles 20a and 20b, trapping the elastic members 28a and 28b, as depicted in FIGS. 5, 6, and 7. FIGS. 5, 6 and 7 depict a preferred embodiment of a garment completed in accordance with the invention. The elastic strips 28a and 28b, sandwiched between folding strips 26a and 26b and noodles 20a and 20b, respectively, serve to form a sealing surface that contacts the skin of the wearer of the garment depicted in FIG. 5. The folding strips may be folded on top of or underneath the noodles.

The garment described in the preferred embodiment of the invention has several advantages. First, it eliminates significant waste in the production of the garment. Instead of being discarded, the noodles can be placed at the crotch of the garment to enhance containment and absorption capability of the disposable garment at the site where such capability is most desired. Second, in a preferred embodiment, the folding strips serve as cuffs that act as leakage control shields and that define, among the crotch of the garment, the cuffs, and the wearer's skin, a trough for receiving excrement. The foregoing noodle cuffs are particularly effective in conjunction with elastic strips operating in conjunction therewith.

The illustrated embodiment is an example of the present invention. Various design contours of the noodles, several folding patterns for the noodles, and several patterns for adhesive are possible within the scope of the invention. For example, the order of folding of the noodles and the folding strips may be varied, as may be the location, if any, of elastic. It will be apparent to one skilled in the art that many embodiments of the invention are possible within the scope of the claims.

I claim:

1. A method of manufacturing a disposable garment from an absorbent pad assembly comprising an interior surface, an exterior surface, two lateral edges and two longitudinal edges, comprising the steps of:

partially cutting a noodle from each longitudinal edge of the absorbent pad assembly, leaving each noodle attached to the absorbent pad assembly at a point proximal to a center point of the assembly;

folding each noodle about the point of attachment toward the interior surface of the absorbent pad assembly to define a trough on the interior surface of the absorbent pad assembly;

affixing each folded noodle to the interior surface of the absorbent pad assembly; and folding an outer edge portion of each noodle back onto the corresponding folded noodle.

2. The method of claim 1, further comprising the step of affixing the folded outer edge portion of each noodle to a surface of the corresponding folded noodle.

3. The method of claim 2, further comprising the step of affixing the folded outer edge portion of each noodle to the interior surface of the absorbent pad assembly.

4. A method of manufacturing a disposable garment from an absorbent pad assembly comprising an interior surface, an exterior surface, two lateral edges and two longitudinal edges, comprising the steps of:

partially cutting a noodle from each longitudinal edge of the absorbent pad assembly, leaving each noodle attached to the absorbent pad assembly at a point proximal to a center point of the assembly;

folding each noodle about the point of attachment toward the interior surface of the absorbent pad assembly to define a trough on the interior surface of the absorbent pad assembly;

affixing each folded noodle to the interior surface of the absorbent pad assembly; and affixing an elastic member proximal to each of the longitudinal edges of the absorbent pad assembly.

5. The method of claim 4, further comprising the step of cutting each elastic member to create discrete elastic areas.

* * * * *